United States Patent
Hunt et al.

(10) Patent No.: US 12,076,271 B2
(45) Date of Patent: Sep. 3, 2024

(54) MEDICAL DEVICES FOR GENERATING HEAT AND METHODS OF TREATMENT USING THE SAME

(71) Applicant: Candesant Biomedical, Inc., San Francisco, CA (US)

(72) Inventors: Niquette Hunt, San Francisco, CA (US); Jacob M. Waugh, Newark, CA (US); Christopher Elkins, Redwood City, CA (US); Jesse Rosen, San Francisco, CA (US)

(73) Assignee: Candesant Biomedical, Inc., San Francisco, CA (US)

( * ) Notice: Subject to any disclaimer, the term of this patent is extended or adjusted under 35 U.S.C. 154(b) by 711 days.

(21) Appl. No.: 17/116,953

(22) Filed: Dec. 9, 2020

(65) Prior Publication Data

US 2021/0169683 A1    Jun. 10, 2021

Related U.S. Application Data

(60) Provisional application No. 62/946,135, filed on Dec. 10, 2019.

(51) Int. Cl.
*A61F 7/03*   (2006.01)
*C08L 23/02*  (2006.01)
(Continued)

(52) U.S. Cl.
CPC ............ *A61F 7/03* (2013.01); *C08L 23/025* (2013.01); *C08L 23/06* (2013.01);
(Continued)

(58) Field of Classification Search
CPC ...... A61F 2007/0226; A61F 2007/0244; A61F 2007/026; A61F 2007/0282; A61F 7/03
See application file for complete search history.

(56) References Cited

U.S. PATENT DOCUMENTS 3,283,357 A   11/1966 Decker et al.
3,400,199 A   9/1968  Balassa
(Continued)

FOREIGN PATENT DOCUMENTS

CN    1299458 A    6/2001
CN    101563113 A  10/2009
(Continued)

OTHER PUBLICATIONS

Non-Final Office Action mailed on Jun. 30, 2023, for U.S. Appl. No. 18/045,399, filed Oct. 10, 2022, 12 pages.
(Continued)

*Primary Examiner* — Tigist S Demie
(74) *Attorney, Agent, or Firm* — COOLEY LLP

(57) ABSTRACT

A device for a medical or cosmetic treatment based on heat is provided. The device includes an impermeable backing layer and an adhesive layer in contact with the backing layer. The device also includes an alkali metal selected from a single, free alkali metal and an alloy alkali metals, the alkali metal in contact with at least a portion of the adhesive layer to define a treatment region. The device also includes a release liner in contact with the adhesive layer and the treatment region. A heat delivery system or kit including the device and a method for its use are also provided.

26 Claims, 7 Drawing Sheets

(51) Int. Cl.
*C08L 23/06* (2006.01)
*A61F 7/02* (2006.01)

(52) U.S. Cl.
CPC ............... *A61F 2007/0226* (2013.01); *A61F 2007/0244* (2013.01); *A61F 2007/0282* (2013.01)

(56) References Cited

U.S. PATENT DOCUMENTS

| | | |
|---|---|---|
| 3,941,128 A | 3/1976 | Bladwin |
| 4,235,332 A | 11/1980 | Andersen et al. |
| 4,274,420 A | 6/1981 | Hymes |
| 4,303,546 A | 12/1981 | Waegerle |
| 4,382,304 A | 5/1983 | Lehmann |
| 4,742,581 A | 5/1988 | Rosenthal |
| 4,796,622 A | 1/1989 | Lu et al. |
| 5,366,492 A | 11/1994 | Ueki |
| 5,879,378 A | 3/1999 | Usui |
| 6,099,556 A | 8/2000 | Usui |
| 6,465,709 B1 | 10/2002 | Sun et al. |
| 6,890,553 B1 | 5/2005 | Sun et al. |
| 6,960,225 B1 | 11/2005 | Zenz et al. |
| 7,084,102 B1 | 8/2006 | Armau |
| 7,097,642 B1 | 8/2006 | Sprague et al. |
| 7,531,080 B2 | 5/2009 | Carson et al. |
| 7,621,110 B2 | 11/2009 | Ota et al. |
| 7,871,508 B2 | 1/2011 | Carson et al. |
| 7,875,066 B2 | 1/2011 | Cohen et al. |
| 7,883,640 B2 | 2/2011 | Doona et al. |
| 8,790,384 B2 | 7/2014 | Uchiyama |
| 10,575,983 B2 | 3/2020 | Waugh et al. |
| 10,980,665 B2 | 4/2021 | Igaue |
| 10,993,833 B2 | 5/2021 | Igaue |
| 11,033,425 B2 | 6/2021 | Waugh et al. |
| 11,241,331 B2 | 2/2022 | Igaue |
| 11,844,668 B2 | 12/2023 | Waugh et al. |
| 2001/0010847 A1 | 8/2001 | Otsuka |
| 2002/0045923 A1 | 4/2002 | Tone et al. |
| 2003/0019508 A1 | 1/2003 | Tomarchio et al. |
| 2004/0042965 A1 | 3/2004 | Usui et al. |
| 2004/0077513 A1 | 4/2004 | Lefenfeld et al. |
| 2004/0146620 A1 | 7/2004 | Iwashita et al. |
| 2005/0000828 A1 | 1/2005 | Carson et al. |
| 2005/0161342 A1 | 7/2005 | Carson et al. |
| 2005/0178061 A1 | 8/2005 | Tonca |
| 2005/0244629 A1 | 11/2005 | Usui et al. |
| 2005/0288646 A1 | 12/2005 | LaVon |
| 2006/0097222 A1 | 5/2006 | Doona et al. |
| 2007/0099812 A1 | 5/2007 | Luizzi et al. |
| 2007/0189940 A1 | 8/2007 | Shurtleff |
| 2007/0267595 A1 | 11/2007 | Dodo |
| 2008/0014481 A1 | 1/2008 | Fiebig |
| 2008/0140165 A1 | 6/2008 | Cohen et al. |
| 2009/0041614 A1 | 2/2009 | Lefenfeld et al. |
| 2009/0062890 A1 | 3/2009 | Ugajin et al. |
| 2009/0181157 A1 | 7/2009 | Toreki et al. |
| 2010/0049178 A1 | 2/2010 | Deem et al. |
| 2010/0087902 A1 | 4/2010 | Ota et al. |
| 2010/0150824 A1 | 6/2010 | Withers-Kirby |
| 2010/0196343 A1 | 8/2010 | O'Neil et al. |
| 2011/0106227 A1 | 5/2011 | Desideric et al. |
| 2012/0022621 A1 | 1/2012 | Wong et al. |
| 2013/0074860 A1 | 3/2013 | Colvan et al. |
| 2013/0085461 A1 | 4/2013 | Leaman et al. |
| 2013/0260623 A1 | 10/2013 | Oh |
| 2014/0031748 A1* | 1/2014 | Usui ............... A61F 7/034 604/113 |
| 2014/0206947 A1 | 7/2014 | Isserow et al. |
| 2015/0184891 A1 | 7/2015 | Oka et al. |
| 2016/0120693 A1 | 5/2016 | Guillon et al. |
| 2016/0131464 A1 | 5/2016 | Rubin |
| 2016/0213294 A1 | 7/2016 | Patton |
| 2016/0242959 A1* | 8/2016 | Waugh ............... A61F 7/03 |
| 2019/0008733 A1 | 1/2019 | Banowski et al. |
| 2020/0121497 A1 | 4/2020 | Shr et al. |
| 2021/0059855 A1 | 3/2021 | Waugh et al. |
| 2021/0093479 A1* | 4/2021 | Robinson ............... B32B 7/12 |
| 2021/0170457 A1 | 6/2021 | Hunt et al. |
| 2021/0205125 A1 | 7/2021 | Mohammadi et al. |
| 2021/0205501 A1 | 7/2021 | Bright |
| 2022/0305278 A1 | 9/2022 | Levin |
| 2023/0113373 A1 | 4/2023 | Waugh et al. |
| 2023/0119652 A1 | 4/2023 | Waugh et al. |

FOREIGN PATENT DOCUMENTS

| | | |
|---|---|---|
| EP | 2 151 171 A1 | 2/2010 |
| GB | 1068667 A | 5/1967 |
| GB | 2 297 490 A | 8/1996 |
| JP | S-53-006088 U | 1/1978 |
| JP | S-60-240784 A | 11/1985 |
| JP | S63168484 A | 7/1988 |
| JP | 2001/212167 A | 8/2001 |
| JP | 2004-504580 A | 2/2004 |
| JP | 2004-065949 A | 3/2004 |
| JP | 2008-113934 A | 5/2008 |
| JP | 2013-176628 A | 9/2013 |
| JP | 2014-090894 A | 5/2014 |
| JP | 2015-029607 A | 2/2015 |
| JP | 2015159899 A | 9/2015 |
| KR | 101416443 B1 | 7/2014 |
| WO | WO-99/41554 A1 | 8/1999 |
| WO | WO 2001/003625 A2 | 1/2001 |
| WO | WO-02/06421 A1 | 1/2002 |
| WO | WO-03/103673 A1 | 12/2003 |
| WO | WO-2008/019051 | 2/2008 |
| WO | WO-2015/016281 A1 | 2/2015 |
| WO | WO-2016/123132 A1 | 8/2016 |
| WO | WO 2016/134245 A1 | 8/2016 |
| WO | WO-2018/206449 A1 | 11/2018 |
| WO | WO-2021/119151 A1 | 6/2021 |
| WO | WO-2021/119192 A1 | 6/2021 |
| WO | WO-2022/234204 A1 | 11/2022 |

OTHER PUBLICATIONS

International Search Report from International Patent Application No. PCT/US2020/064105, 6 pages, International Search Report mailed Apr. 12, 2021.

Pulyalina et al., "Improved Hydrogen Separation Using Hybrid Membrane Composed of Nanodiamonds and P84 Copolyimide", Polymers, vol. 10, No. 828, 12 pages (2018).

Extended European Search Report mailed on Dec. 18, 2020, for EP Application No. 20 193 817.2, filed on Feb. 19, 2016, 7 pages.

Final Office Action mailed on Mar. 26, 2019, for U.S. Appl. No. 15/048,052, filed Feb. 19, 2016, 14 pages.

Hamm, H. et al. (2006). "Primary focal hyperhidrosis: disease characteristics and functional impairment," Dermatology 212:343-353.

Hornberger, J. et al. (2004). "Recognition, Diagnosis, and Treatment of Primary Focal Hyperhidrosis," J. Am. Acad. Dermatol. 51:274-286.

International Search Report mailed on May 23, 2016, for PCT Application No. PCT/US2016/018655, filed on Feb. 19, 2016, 4 pages.

International Search Report mailed on Mar. 9, 2021, for PCT Application No. PCT/US2020/064049, filed on Dec. 9, 2020, 5 pages.

Naumann, M.K. et al. (2002). "Effect of botulinum toxin type A on quality of life measures in patients with excessive axillary sweating: a randomized controlled trial," Br. J. Dermatol. 147:1218-1226.

Non-Final Office Action mailed on Oct. 1, 2018, for U.S. Appl. No. 15/048,052, filed Feb. 19, 2016, 22 pages.

Non-Final Office Action mailed on Jun. 26, 2019, for U.S. Appl. No. 15/048,052, filed Feb. 19, 2016, 16 pages.

Non-Final Office Action mailed on Oct. 24, 2019, for U.S. Appl. No. 15/048,052, filed Feb. 19, 2016, 15 pages.

Non-Final Office Action mailed on May 3, 2023, for U.S. Appl. No. 18/045,396, filed Oct. 10, 2022, 17 pages.

(56) References Cited

OTHER PUBLICATIONS

Notice of Allowance mailed on Jan. 7, 2020, for U.S. Appl. No. 15/048,052, filed Feb. 19, 2016, 11 pages.
Notice of Allowance mailed on Feb. 18, 2021, for U.S. Appl. No. 16/780,736, filed Feb. 3, 2020, 11 pages.
Rao, W. et al. (2008). "Tumor thermal ablation therapy using alkali metals as powerful self-heating seeds," Minim. Invasive Ther. Allied Technol. 17:43-49.
Rao, W. et al. (2009). "Injectable liquid alkali alloy based-tumor thermal ablation therapy," Minim. Invasive Ther. Allied Technol. 18:30-35.
Strutton, D.R. et al. (2004). "US prevalence of hyperhidrosis and impact on individuals with axillary hyperhidrosis: results from a national survey," J. Am. Acad. Dermatol. 51:241-248.
Teale, C.W. et al. (2002). "Development, validity, and reliability of the hyperhidrosis impact questionnaire (HHIQ)," Qual. Life Res. 11:702.
Written Opinion of the International Searching Authority mailed on May 23, 2016, for PCT Application No. PCT/US2016/018655, filed on Feb. 19, 2016, 8 pages.
Written Opinion of the International Searching Authority mailed on Mar. 9, 2021, for PCT Application No. PCT/US2020/064049, filed on Dec. 9, 2020, 7 pages.
Written Opinion of the International Searching Authority mailed on Apr. 12, 2021, for PCT Application No. PCT/US2020/064105, filed on Dec. 9, 2020, 8 pages.
Final Office Action mailed on Aug. 23, 2023, for U.S. Appl. No. 18/045,396, filed Oct. 10, 2022, 14 pages.
Non-Final Office Action mailed on Aug. 29, 2023, for U.S. Appl. No. 17/095,514, filed Nov. 11, 2020, 19 pages.
Notice of Allowance mailed on Oct. 17, 2023, for U.S. Appl. No. 18/045,399, filed Oct. 10, 2022, 8 pages.

\* cited by examiner

MEDICAL DEVICES FOR GENERATING HEAT AND METHODS OF TREATMENT USING THE SAME

CROSS REFERENCE TO RELATED APPLICATIONS

The application claims the benefit of U.S. Provisional Application No. 62/946,135, filed Dec. 10, 2019, incorporated herein by reference in its entirety.

TECHNICAL FIELD

The technology described herein generally relates to methods and devices to use and dispose of alkali metal patches in a therapeutic procedure that includes generating heat in a selected treatment region for medical and/or cosmetic purposes.

BACKGROUND

Devices that rely on an exothermic reaction as a self-contained heat source are familiar to consumers in the form of, for example, disposable hand and foot warmers. These devices include a reaction mixture that generates heat when water or oxygen is introduced into the reaction mixture.

Devices that produce heat are also used in medical situations, such as in the ablation of tissues or cells, to cauterize wounds. Cauterization is a medical technique used to stop blood flow and help seal the surface of a wound. Various conventional devices for carrying out cauterization include electro-cauterizers and laser cauterizers that act to destroy tissue while rapidly aiding the coagulation of blood vessels which have been cut in the wound. These cauterizing devices do not rely on an exothermic chemical reaction as the source of heat.

Heat can also be used to render surfaces aseptic. For example, a variety of devices and methods have been used to sterilize surgical instruments (such as autoclaves) and other surfaces, such as a patient's skin or a surgeon's hands, and examples of such devices that are non-heat based include antiseptic wipes, antibacterial solutions, and the like. Sterilization techniques for instruments generally use heat for extended periods of time as an aid in destroying bacterial and other pathogens on the instruments. Sterilization techniques for use with human skin or other surfaces typically rely on a chemical interaction between the material being applied and the pathogens themselves to destroy the pathogens.

Medical systems such as bandages are conventionally used to slow bleeding by providing pressure to a wound and by assisting with the blood's natural coagulation process that involves platelets in the blood and fibrin. Bandages are also used to help prevent additional bacterial and other harmful materials from entering an open wound. Bandages used to cover wounds generally include a portion either directly coupled to the bandage or coupled to the wound through the bandage that is sterile, such as a gauze pad or other sterile structure.

A device that comprises a reactant that is capable of generating heat by an exothermic reaction with a reactant in or on a treatment site, such as human skin or tissue is desired. Such a device is desired for use in various applications, such as treating certain disorders that respond to a burst of heat, for use in treating skin disorders, and for sterilizing areas of skin for treatment.

SUMMARY

In a first aspect, a device comprising an impermeable backing layer and an adhesive layer in contact with the backing layer is provided. The device also comprises an alkali metal selected from a single alkali metal and an alloy of alkali metals, the alkali metal in contact, directly or indirectly, with at least a portion of the adhesive layer to define a treatment region, and a release liner in contact with the adhesive layer and the treatment region.

In a second aspect, a heat delivery system comprises a container that is essentially impermeable to water, oxygen, or both, and a device removably disposed in the container. The device comprises a backing layer, an adhesive layer and an alkali metal selected from a single alkali metal and an alloy of alkali metals. The alkali metal contacts the adhesive layer to define a treatment region. The device also includes a removable release liner in contact with the adhesive layer.

In a third aspect, a kit comprises a heat delivery system including a device removably disposed in a container that is essentially impermeable to water, oxygen, or both, the device including a backing layer, an adhesive layer, and an alkali metal selected from a single alkali metal and an alloy of alkali metals, the alkali metal contacts the adhesive layer to define a treatment region. The kit also optionally comprises one or more wipes, optionally including a solvent or reagent. The kit also comprises a means for disposal of the device.

In yet another aspect, a method for treatment of hyperhidrosis comprises providing a heat delivery system including a device removably disposed in a container that is essentially impermeable to water, oxygen, or both. The device comprises a backing layer, an adhesive layer, and an alkali metal selected from a single alkali metal and an alloy of alkali metals, the alkali metal in contact with the adhesive layer to define a treatment region. The device also comprises a release liner in contact with the treatment region. The method comprises removing or instructing to remove the release liner and applying or instructing to apply the device to skin or tissue of a human subject in a manner to contact the treatment region with skin or tissue at a treatment site, wherein moisture on or in the skin or tissue reacts with the alkali metal to generate heat in an amount to provide a reduction in production of sweat at the treatment site.

DETAILED DESCRIPTION

Figure 1A:
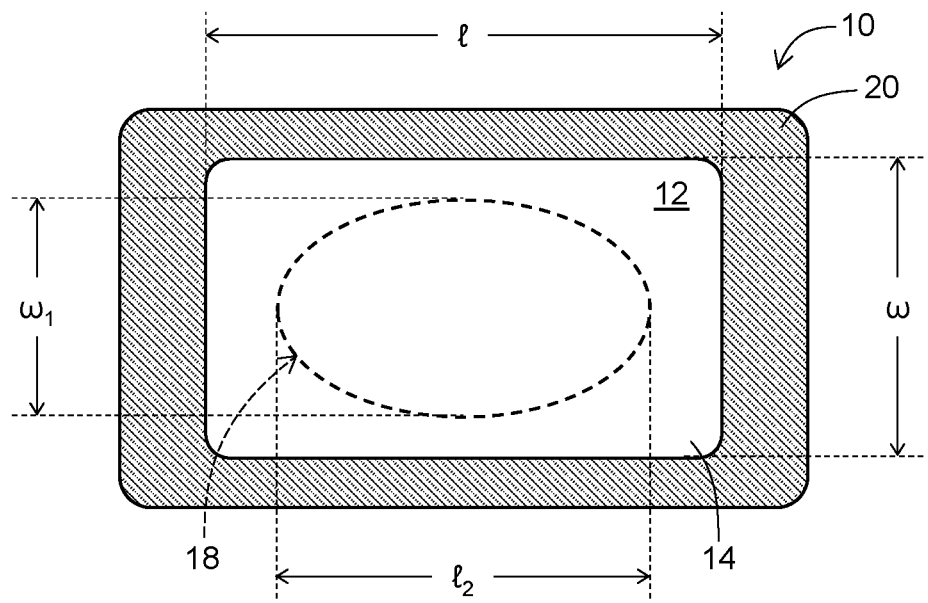
FIGS. 1A-1C illustrate a plan view (FIG. 1A) and cross sectional views (FIGS. 1B-1C) of a device for generating heat in a desired treatment region, for contact with a treatment site on a human body for medical and/or cosmetic purposes, according to some embodiments.

Devices as disclosed herein include an alkali metal (e.g., lithium, sodium, potassium, rubidium, cesium, francium, or any alloy of the above) to enable an approach for effective treatment of certain skin conditions, such as hyperhidrosis (the profusion of sweat) or other medical or aesthetic dermatological conditions. The reaction of the alkali metal with moisture in or on the skin or tissue at a treatment site creates an amount of heat for a therapeutic or cosmetic purpose.

The devices can also be used to substantially sterilize or render substantially aseptic a surface—a human skin or tissue surface or any other surface, such as a surgical instrument, a laboratory bench top surface, or a petri dish. Approaches for safe and easy disposal of the devices are also provided, whether the device is used in a controlled environment of a healthcare facility (e.g., hospital, clinic, doctor's office), in a laboratory, or in a home setting.

The alkali metal is present in the devices in an amount sufficient to generate heat, the heat generation occurring when the alkali metal contacts water or another oxidizer. Typically, the alkali metal contacts water or another oxidizer when the alkali metal is applied to a treatment surface, as will be described herein below. As used herein, an 'alkali metal' intends a univalent (monovalent) metal belonging to group 1A or an alloy of such metals of the periodic table that is essentially or substantially in free form, or in its pure or neat form. These alkali metals include potassium, sodium, lithium, rubidium, cesium, and francium. As can be appreciated, the reactive nature of the free alkali metals results in a portion of the free alkali metal reacting with oxygen to form an oxide. Thus, reference herein to an alkali metal in free form, or an alkali metal in pure form, contemplates that the free or pure alkali metal may comprise a minor fraction that is oxidized. References to 'alkali metal' or to one of the specific metals, e.g., potassium metal or sodium metal, include its oxides, peroxides, superoxides, hydroxides, provided the alkali metal in the presence of water undergoes an exothermic reaction. Reference to a 'salt of an alkali metal' intends a compound of an alkali metal and another element, such as sodium chloride, potassium chloride, sodium carbonate, which are water soluble and generally do not react exothermically with water. An alkali metal alloy intends a combination of two or more pure or free alkali metals.

When the alkali metal reacts with water, e.g., during use of the device when the alkali metal contacts moisture, sweat or other source of water, energy (e.g., heat) is generated from the exothermic reaction between water and the alkali metal. In an embodiment, the moisture, sweat, or other source of water for reaction with the alkali metal that is in, on, or otherwise associated with the device, is separate from the device itself. The energy is transferred to the treatment surface, such as a skin or body surface of a human, to provide a clinical or cosmetic benefit. In some embodiments, the device, also referred to herein as a patch, is configured for a single use and to be disposable, and the single use may leave a portion of the alkali metal unreacted—e.g., a portion of the alkali metal remains capable of reaction with water. Accordingly, in some embodiments, a simple, safe way to react the unused or unreacted portion of alkali metal is provided, to render it safe so that it may be disposed of with conventional methods (e.g., mixed into a solution that can be drained or placed in a garbage container).

In one embodiment, the alkali metal is potassium or sodium. In another embodiment, the alkali metal is a neat alkali metal, sometimes referred to as the free metal, such as potassium free metal or sodium free metal. In other embodiments, the alkali metal is potassium or sodium in the form of an oxide. Sodium monoxide ($Na_2O$), sodium peroxide ($Na_2O_2$), and sodium superoxide ($NaO_2$) are examples. Sodium metal is a soft metal that is highly reactive with oxygen and water. Sodium metal can be cut, broken up, and shaped into various forms due to its softness. Potassium metal is likewise a soft metal that has higher reactivity with oxygen and water than does sodium metal. In one embodiment, the alkali metal is a solid or a semi-solid at room temperature (e.g., about 25° C.).

In another embodiment, the alkali metal is an alloy, such as an alloy of sodium and potassium. Sodium metal and potassium metal can be combined to form a sodium/potassium alloy (NaK) which is a liquid at room temperature. NaK that is liquid at room temperature contains between about 40% to about 90% potassium by weight. A eutectic between sodium and potassium occurs at about 77% potassium and about 23% sodium and the liquid metal at the eutectic point is less dense than water. Eutectic compositions may be used in various embodiments of the devices described herein, as well as any combination of sodium and potassium in proportions that form a stable alloy. Accordingly, the term "NaK" is used herein to refer to a sodium and potassium alloy, and this term represents any possible combination of sodium and potassium and not just a 50/50 atomic mixture and not just a eutectic composition. In one embodiment, the alkali metal alloy is a solid or a semi-solid at room temperature (e.g., about 25° C.).

A reaction of an alkali metal compound (e.g., sodium, Na; potassium, K) with water (e.g., the "reactant" or "solubilizer") may be described with the following chemical equation:

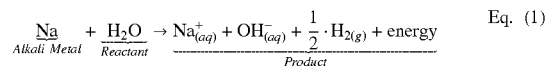

$$\underset{\text{Alkali Metal}}{\underline{Na}} + \underset{\text{Reactant}}{\underline{H_2O}} \rightarrow \underset{\text{Product}}{Na^+_{(aq)} + OH^-_{(aq)} + \frac{1}{2} \cdot H_{2(g)} + \text{energy}} \qquad \text{Eq. (1)}$$

The reaction in Eq. 1, where Na is used as an example for illustrative purposes only, is highly exothermic. Methods and devices as disclosed herein exploit the above heat generation (e.g. energy) effect for therapeutic purposes in a desired treatment region of a patient. In addition, after use of devices or patches as disclosed herein, some embodiments provide various solutions to convert the alkali metal residue in a used device or patch into another, non-pyrophoric substance, such as a metal hydroxide, a metal alkoxide, or a salt (e.g., an alkali-halide such as NaCl, and the like).

Figure 1B:
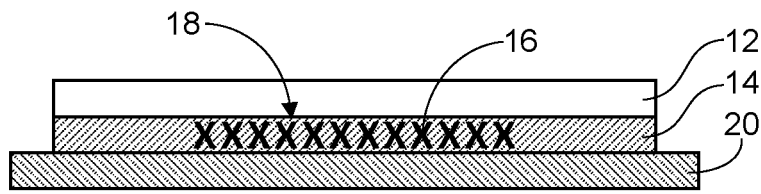
Figure 1C:
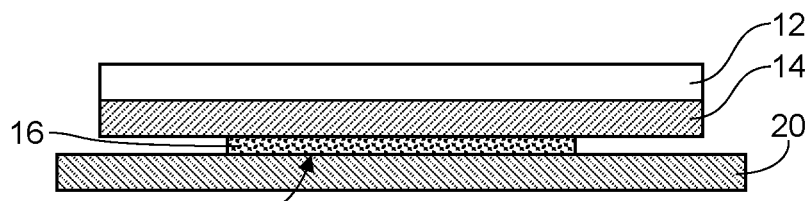

FIGS. 1A-1C illustrate a plan view and cross-sectional views (FIGS. 1B-1C) of embodiments of a device 10 for generating heat. Device 10 is in the form of a wearable patch that comprises a backing layer 12, an adhesive layer 14 in contact with the backing layer, and an alkali metal 16. The alkali metal is, in certain embodiments, selected from a single, free alkali metal that is essentially or substantially pure and an alloy of alkali metals, each alkali metal in the alloy being a free alkali metal. In some embodiments, the alkali metal or alloy is essentially or substantially a pure or free alkali metal, which intends that the free alkali metal on a weight basis is at least about 80%, 81%, 82%, 83%, 84%, 85%, 86%, 87%, 88%, 89%, 90%, 91%, 92%, 9%3, 94%, 95%, 96%, 97% or 98% free alkali metal, wherein the balance is the alkali metal(s) in oxidized or hydroxide form. The alkali metal is in contact with at least a portion of the adhesive layer to define a treatment region 18. Treatment region 18 is shown in phantom in FIG. 1A, as in the plan view of FIG. 1A backing layer 12 obscures the alkali metal 16, unless the backing layer is transparent. The patch in this embodiment also comprises a release liner 20 in contact with the adhesive layer. In one embodiment, the alkali metal, adhesive layer, and backing layer form a treatment device that is essentially planar and that is applied to a treatment surface, such as a surface on a human body, wherein each layer of the treatment device (alkali metal, adhesive layer, and backing layer) remains in contact with the other during application and use of the device. In one embodiment, the device is not a syringe or a needle.

In some embodiments, alkali metal 16 is selected from pure sodium and pure potassium. In some embodiments, the alkali metal may include an alloy of pure (or free) alkali metals selected from sodium and potassium. In some embodiments, the alkali metal and the alloy may be partially in oxide form. For example, in some embodiments, it may be unavoidable that a small amount of the alkali metal be oxidized. In some embodiments, the alkali metal includes a population of particles embedded in a matrix, which can be the adhesive matrix 14, as seen best in FIG. 1B. In other embodiments, the alkali metal can be a layer that is in contact with the adhesive layer 14, as seen in FIG. 1C. As depicted in FIG. 1C, alkali metal 16 is in direct contact with adhesive layer 14. In other embodiments, not shown, alkali metal 16 and adhesive layer 14 are in indirect contact with one or more intervening layers disposed between the alkali metal and the adhesive layer. In one embodiment, the alkali metal 16 is a continuous layer or film (or foil, discussed below) with first and second surfaces. A support material is secured to one of the first and second surfaces. For example, a support material in the form of an adhesive laminate is placed directly on one side of the alkali metal layer to form a composite of alkali metal layer and adhesive laminate. Backing layer 12, which itself may be a laminate of an adhesive and a backing material (e.g., paper, fabric, non-woven, foil, foam, plastic film, polymeric film), is secured to the composite to form the device.

In some embodiments, the layer of alkali metal is a foil, which intends that the alkali metal is in the form of a metal sheet. In some embodiments, the alkali metal 16 is a continuous layer of any desired dimensions. In one embodiment, the layer of alkali metal has a thickness of between about 0.01-8 mm, 0.01-6 mm, 0.01-5 mm, 0.015-5 mm, 0.02-5 mm, 0.02-4.5 mm, 0.02-4 mm, 0.02-3.5 mm, 0.02-3 mm, 0.02-2.5 mm, 0.025-5 mm, 0.025-4.5 mm, 0.025-4 mm, 0.025-3.5 mm, 0.025-3 mm, 0.025-2.5 mm, 0.03-5 mm, 0.03-4.5 mm, 0.03-4 mm, 0.03-3.5 mm, 0.03-3 mm, or 0.03-2.5 mm. In other embodiments, the layer is of any desired thickness or is of any desired geometric shape, such as oval square, rhombus, parallelogram, circle, crescent, triangular, octagon, heptagon, rectangular, and the like. The patch can also be shaped to mirror or mimic a target body part or a portion thereof, and, accordingly, in one embodiment, the patch is shaped as a palm, a finger, a hand, an underarm, a sole of a foot, or a portion of any of the foregoing. In another embodiment, the patch is comprised of a plurality of individual patch portions, each portion with an individual shape, where the portions are configured to be arranged to mirror or mimic a desired shape. The desired shape can be any geometric shape, such as those mentioned above, or can be a body part shape. The individually shaped portions can be the same or different shapes, provided that when arranged collectively they are capable for achieving a desired shape.

The shape or dimensions of the alkali metal layer defines a treatment region that is intended to contact a skin surface, tissue surface or other surface to receive a heat treatment, as will be described below. In one embodiment, the treatment region has a length and a width or the treatment region has a diameter, and the backing layer has a length and a width, or the backing layer has a diameter, that is greater than the length and width, or the diameter, of the treatment region. This embodiment is illustrated in the various embodiments of the device shown in FIGS. 1A-1C, where backing layer 12 has a length l and a width w that is greater than length $l_1$ and width $w_1$ of the oval-shaped treatment region 18. In one embodiment, one or more dimensions of the backing layer, e.g., the length, width, and/or diameter, is 10%, 15%, 20%, 25% or 30% greater than one or more dimensions of the backing layer, e.g., the length, width, and/or diameter of the treatment region. In embodiment, the device is planar. In one embodiment, the adhesive layer that is in contact with the alkali metal is a planar adhesive layer.

It will be appreciated that the dimensions of the treatment region can be selected and optimized for a treatment site on a body. For example, the treatment region may be designed for contact with a treatment site that is an axilla (under arm), chest, palm of a hand, sole of a foot, groin, or the forehead. The treatment region of the device can be the same or different geometry or dimensions from any other layer of the device. For example, the treatment region has a geometry and the backing layer has a geometry, and the treatment region geometry may be different from the backing layer geometry. For example, in some embodiments, the treatment region has an oval geometry and the backing layer has a rectangular geometry. The treatment region has an area and the backing layer has an area that may not be the same, although they overlap. For example, in some embodiments, the treatment region area is at least 10% smaller than the backing layer area.

Figure 2A:
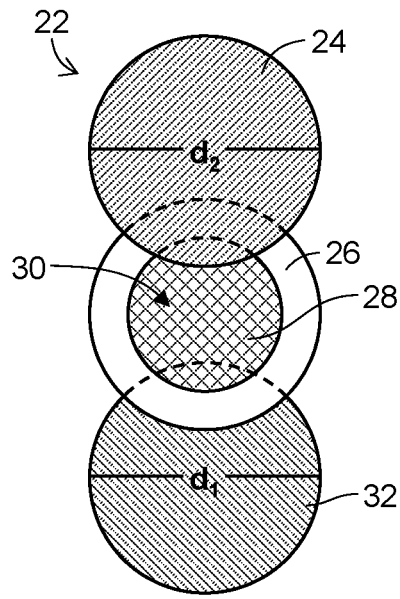
FIGS. 2A-2B illustrate exploded views of embodiment of a device for generating heat, illustrating multiple layers of materials, according to some embodiments.
Figure 2B:
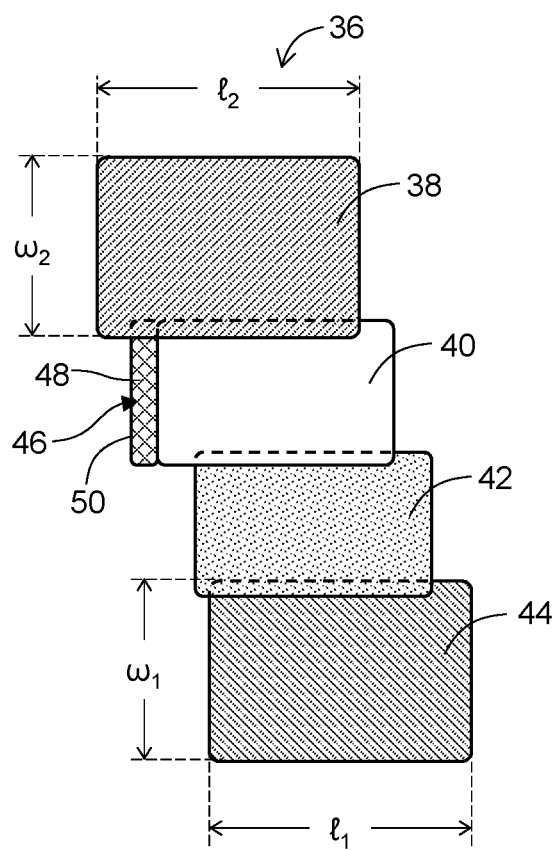

The release liner of the device has a length and a width or a diameter that is the same as or greater than the length and width or the diameter of the treatment region. With reference to FIG. 2A, a device 22 is comprised of a backing layer 24, an adhesive layer 26 that directly or indirectly contacts the backing layer, and an alkali metal 28 in contact with at least a portion of the adhesive layer. The area over which the alkali metal is dispersed or extends on the adhesive layer defines a treatment region 30, which in the embodiment of FIG. 2A is a circular region. A release liner 32 is dimensioned to have essentially the same dimensions of the adhesive layer 26. In this embodiment, the release liner is also of essentially the same dimensions as the backing layer. Release liner 32 has a diameter $d_1$ that is essentially the same as diameter $d_2$ of the backing layer. The release liner is removed by a user of the device, to expose the treatment region 30 and the adhesive layer 26. The adhesive layer can be a peripheral adhesive about the treatment region, or can be a continuous adhesive layer wherein alkali metal foil or particles are laminated or embedded in a portion of the adhesive layer, thus defining a treatment region. In the embodiment of FIG. 2B, a device 36 is comprised of a backing layer 38, an adhesive matrix 40, an alkali metal foil 42, and a release liner 44. Release liner 44 has a length $l_1$ and a width $w_1$ and backing layer 38 has a length $l_2$ that is less than the length $l_1$ of the release liner. Backing layer 38 also has a width $w_2$ that is essentially the same as the width $w_1$ of the release liner. In some embodiments, the release liner has a length and a width or a diameter that is greater than the length and width or the diameter of the adhesive layer. In some embodiments, the release liner and the backing layer have essentially the same length and width or essentially the same diameter, in both cases greater than the length and width or the diameter of the treatment region. In some embodiments, the release liner may be in contact with the adhesive layer and may cover the treatment region. Furthermore, in some embodiments, the release liner may extend to or beyond the boundaries of the adhesive layer and cover the treatment region.

The device of FIG. 2B also includes a release tab or lift tab 46 to ease separation of the release liner from the device. Tab 46 corresponds, in one embodiment, to a portion of the adhesive layer that is covered with a non-adhesive material. Tab 46 in other embodiments is created using a paper or material that has opposing sides, such as an upper side 48 and a lower side 50, wherein one or both of the upper side and lower side is treated with a material that is non-adherent or adherent for the adhesive layer.

The backing layer of the devices described herein is generally of a material that is water impermeable, oxygen impermeable or both water and oxygen impermeable. The backing layer can be transparent or colored. In some embodiments, the backing layer is stretchable to accommodate the wearable device in a desired portion of the body. In one embodiment, a streatchable backing layer is also water, oxygen or both impermeable, is a laminate of a woven or non-woven fabric and an impermeable material, where the woven or non-woven fabric is capable of being made longer or wider by at least about 2.5, 3, 35, 4, or 5% in one or more directions. For example, in some embodiments, the backing layer is a transparent, adhesive coated polyolefin. The polyolefin can be polyethylene, polypropylene, polymethylpentene, polybutene, as well as olyolefin elastomers such as polyisobutylene and ethylene propylene rubber. The backing layer may comprise an adhesive, such as an acrylate adhesive. The backing layer has opposing sides, and the adhesive layer is coated on one side of the backing layer.

The adhesive layer in the devices described herein is generally a pressure-sensitive adhesive. The pressure-sensitive adhesive layer may include a hydrophobic adhesive. The hydrophobic adhesive is formed from an acrylic acid monomer or an acrylate monomer. The acrylate monomer is selected from the group consisting of methylacrylate, methylmethacrylate, ethyl acrylate, 2-ethylhexyl acrylate, hydroxyethyl methacrylate, butyl acrylate, butyl methacrylate, and 2-cholorethyl vinyl ether. The hydrophobic adhesive is a polyacrylate.

The alkali metal is laminated to, incorporated into, embedded in or in contact with the adhesive layer. In some embodiments, the alkali metal is positioned in or on the adhesive layer for contact with the skin of a patient or subject for medical or cosmetic treatment. The alkali metal may be adhered as a foil layer to the pressure-sensitive adhesive layer. The alkali metal may be dispersed in on or embedded in or on an adhesive matrix that is in contact with the pressure-sensitive layer.

The release liner in the devices described herein is generally a thermoplastic polyolefin material or a polyester material with opposing sides, one side coated with a releasable coating material. The polyolefin material may include polyethylene or polypropylene. In some embodiments, the polyester material is polyethylene terephthalate. In some embodiments, the releasable coating material comprises a silicone.

As mentioned above, in some embodiments the device or the release liner may include a lift tab to facilitate placing of the wearable patch in a desired bodily area. The lift tab may be created by insertion of a material between an edge portion of the adhesive layer and the release liner. In some embodiments, the lift tab material has opposing sides, wherein one of the opposing sides is coated with a non-adherent material for the adhesive layer. The lift tab material has opposing sides, wherein at least one of the opposing sides may be coated with an adherent material for the adhesive layer.

Figure 3:
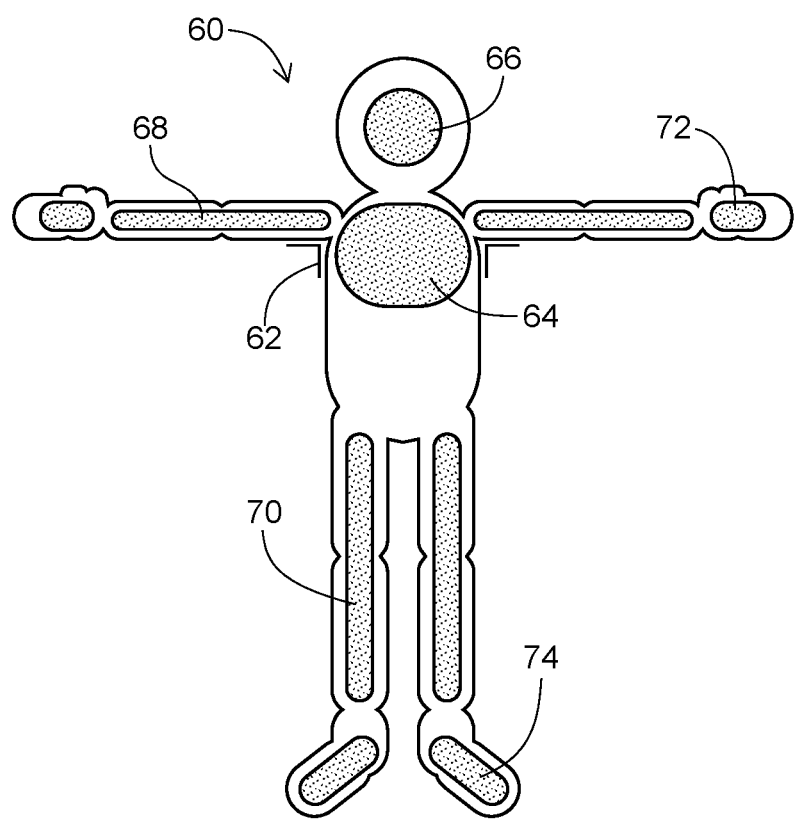
FIG. 3 illustrates a human body and treatment sites where a heat generating device may be applied, according to some embodiments.

FIG. 3 illustrates a human body 60 and multiple treatment regions where the devices described herein may be applied, according to some embodiments. The treatment regions may include an arm pit 62, the chest 64, and an area on the face 66 (e.g. for cosmetic applications) such as the forehead, under eye region, cheek, chin, etc. In some embodiments, a device as disclosed herein can be applied on any extremity, such as an arm 68, a leg 70, a hand 72, and a foot 74. More generally, a device for medical or cosmetic treatment using heat, as disclosed herein, may be used in wounds, cuts, rashes, and other cutaneous lesions in any portion of a bodily surface. It may also be applied to intact, unbroken skin or tissue, including mucosal tissue.

Figure 4:
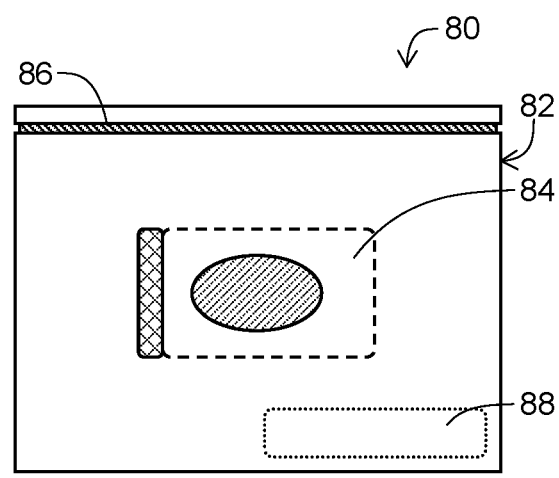
FIG. 4 illustrates a system comprising a heat generating device, according to some embodiments.

FIG. 4 illustrates a system 80 that includes a container 82 and a device 84 as described herein for a medical or cosmetic treatment using heat. The container is openable by a user, such as via a sealed opening 86 along an edge or side of the container. Device 84 is removably disposed in the container. The container is preferably a protective container, intending that the container protects the device from contact with oxygen and/or water (moisture) by virtue of being impermeable to water and/or oxygen. The sealed opening 86 is sealed such that it is also water and/or oxygen impermeable. In some embodiments, the removable seal includes a hermetic seal, such as a zip-lock. The device may be a wearable patch including a backing layer, an adhesive layer, and an alkali metal selected from a single free alkali metal and an alloy of two or more free alkali metals, as described herein. The system may also include instructions for use 88, for example, in the form of a printout with handling instructions, guiding a user to apply and dispose of the device. In some embodiments, the instructions 88 may include a printed barcode or a Quick Response (QR) code that the user may scan with a smart phone to access a network resource. The network resource may include identifying information for the device, handling instructions, disposal instructions, and/or other data of interest or relevance for the user, such as inventory data, and health and safety information of the materials and methods of use of the device.

Figure 5:
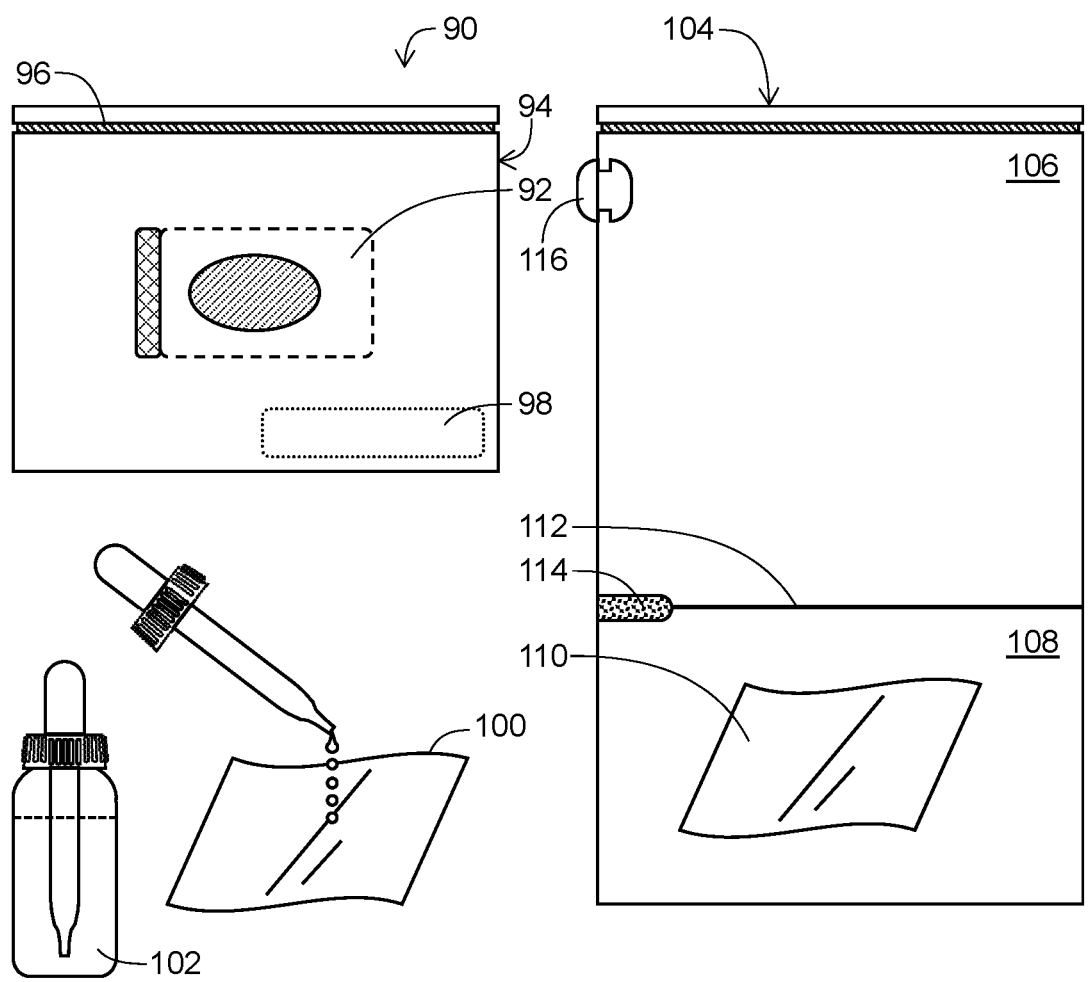
FIG. 5 illustrates a kit including a heat generating device, for a medical or cosmetic treatment using heat, according to some embodiments.

FIG. 5 illustrates a kit 90 that is comprised of a heat-generating device 92 as described herein in a protective container 94, as described in FIG. 4, The impermeable container may comprise a removable or openable seal 96 to enable the user to access the device and, optionally, instructions for use 98. The kit optionally includes a wipe 100 and/or a solvent 102, where the wipe and solvent can be separate (as shown) or combined (e.g., the solvent is on or within the wipe). In one embodiment, the wipe and/or solvent are provided in the kit for cleansing and/or treating a treatment site on a subject prior to heat treatment with the device in the kit. In an embodiment, an essentially dry wipe that is capable of absorbing waster or moisture from a treatment surface is provided in the kit, where the wipe is, for example, a disposable absorbent pad or substrate, a woven, knitted or non-woven cloth or fabric, articles made of natural or synthetic fibers, and other articles that absorb water. In another embodiment, a wipe that is pre-moistened with a cleaning reagent or solvent is included in the kit. The pre-moistened wipe can be packaged in a pouch or liquid tight packaging unit, for opening by a user or medical provider. In an embodiment, the cleansing reagent or solvent does not foam or lather upon application to the treatment site. Solvents or reagents for treating or cleansing a treatment site may be any solvent or reagent suitable for application to skin that removes, for example, dirt, debris, oils, cosmetics, and/or bacteria. In one embodiment, the pre-moistened wipe is essentially water-free. The wipe may be pre-moistened with, or the solvent or reagent in the container, can be an alcohol, such as isopropyl alcohol or ethanol, In another embodiment, the kit optionally comprises a cleanser and a wipe for cleaning the treatment site on the subject after heat treatment with the device in the kit. The cleanser and wipe can be present in the kit as separate components, for example, a vial or bottle with a cleanser and a separate wipe, such as a gauze, woven or non-woven fabric, or absorbent substrate. The cleanser and wipe can be combined to form a cleansing wipe where the cleanser is on or within the wipe. The cleansing wipe may be packaged in a sealed, fluid tight container that a user opens to remove the cleansing wipe, which may be partially or fully saturated with the cleanser. In one embodiment, the kit comprises a wipe and a solvent (combined or as separate components) for cleansing and/or treating a treatment site on a subject prior to heat treatment with the device in the kit and a second cleanser and wipe (combined or as separate components) for cleaning the treatment site on the subject after heat treatment with the device in the kit. In another embodiment, the kit comprises a single wipe and solvent (combined or as separate components) that is suitable for cleansing and/or treating a treatment site on a subject both prior to and after heat treatment with the device in the kit. In another embodiment, the single wipe and solvent (combined or as separate components) is suitable for cleansing and/or treating a treatment site on a subject either prior to or after heat treatment with the device in the kit.

In one embodiment, the kit comprises a wipe and a solvent or reagent (combined or as separate components) that neutralizes a reaction product (discussed above) generated during treatment with the device and deposited on the skin or mucosal surface during treatment. In particular, a hydroxide is generated during use of the device and may remain on the treatment surface. For example, the reaction product may be sodium hydroxide or potassium hydroxide, based on the alkali metal used in the device. The kit and methods described herein may comprise a solvent or reagent that removes, neutralizes, and/or decreases the pH of the hydroxide reaction product. Examples of solvents or regents include weak acids, such as citric acid and acetic acid.

The kit also comprises, in some embodiments, a disposal container 104 for disposing of the device after use. Disposal container 104 comprises a sealable compartment 106 dimensioned to receive a used device, and a reagent compartment 108. The reagent compartment contains or is configured to receive and contain a reagent 110, which can be placed on a carrier or can be placed directly in the reagent compartment. In one embodiment, the wipe 100 and solvent 102 provided in the kit for use in the disposal container, where the wipe is a carrier for the solvent that is a reagent, further described below. In this embodiment, the wipe soaked in the solvent can be placed by a user into the reagent compartment 108 of the disposal container. A wall 112 separates the sealable compartment 106 from the reagent compartment 108, where wall 112 is preferably impermeable to the reagent. The wall may include a reagent permeable region 114, such as a porous membrane that permits passage of the reagent placed on the carrier (wipe) to permit the reagent to enter the sealable compartment once a used device is placed therein. The reagent, in one embodiment, is a solvent that vaporizes at or above room temperature, and the reagent molecule permeate across the permeable region of the wall to enter the sealable compartment. The reagent is selected to be one that reacts with the unreacted alkali metal in the device, in order to react with and neutralize the unreacted alkali metal to permit safe disposal thereof. In some embodiments, the sealable compartment includes a one-way valve 116 that allows any gases generated from reaction of the alkali metal with the reagent solvent (e.g. $H_2$, cf. Eq. 1) to exit the sealable compartment.

Figure 6:
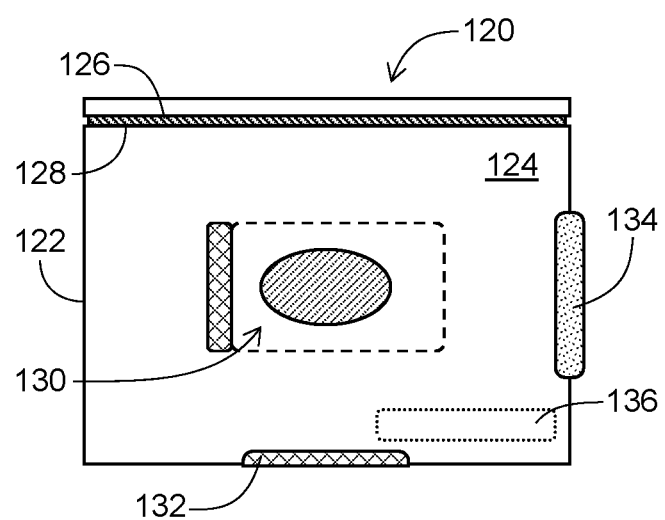
FIG. 6 illustrates a kit for disposing of a heat generating device after use, according to some embodiments

The disposal container of the kit is further described with reference to FIG. 6. FIG. 6 illustrates a disposal kit 120 for disposing of a used device that comprises unreacted alkali metal after use. The disposal kit may be configured as a single-use disposal unit (e.g., the user disposes of at least a portion of the kit after the used patch is neutralized). In some embodiments, the disposal kit may be configured to receive and neutralize multiple used devices before the disposal kit itself is discarded. In yet other embodiments, the disposal kit may be configured to receive and neutralize multiple used devices that are removed from the disposal kit when, for example, an indicator means signals that it is safe to do so. In such embodiments, the used, neutralized alkali devices may be removed from the disposal kit and safely discarded to allow the continued introduction of further used devices.

Kit 120 comprises a disposal container 122 with walls that define a cavity 124 and an opening 126 configured to receive the device into the cavity. In some embodiments, the disposable container is substantially impermeable to water and/or to air and has a closeable or resealable opening 128. In some embodiments, the closeable or resealable opening 128 includes a sliding lock (e.g., a Ziploc top) or screw cap to seal a used device 130 in the disposal container. In some embodiments, the disposal container is manufactured at least in part from a water-permeable material. In some embodiments, the disposal container may include a polyethylene or polypropylene vial or a polyolefin bag. Further, in some embodiments, the disposal container may include at least one or more walls (e.g., a front wall and a rear wall), where the bottom wall is attached to the front and rear walls. In some embodiments, the disposal container further includes two side walls, where each side wall is connected to the front wall, the rear wall and to the bottom wall, wherein at least one wall is flexible. In some embodiments, at least one of the walls is circular or curved, and the disposal container includes an annular or a circular cavity. In some embodiments, at least one of the walls in the container may include a metal, a metal foil (e.g., stainless steel), a polyolefin (e.g., polyethylene terephthalate) or a metal-sputtered plastic film.

In some embodiments, the disposal container comprises a reactant 132 that chemically reacts with the unused, unreacted alkali metal in the used device to neutralize the unused, unreacted alkali metal for safe disposal thereof. The reactant may be a solvent that is miscible with water and that dissolves the alkali metal. The solvent may include an alcohol or a glycol, wherein the alcohol is selected from ethanol, isopropanol, t-butanol, stearyl alcohol, and tris(trimethylsilyl)methanol, and the glycol can be, for example, propylene glycol. In some embodiments, the reactant may be a substantially anhydrous R—OH (~99%) solution, where R is an unspecified chemical group. For example, in some embodiments, the reactant may include ethanol, isopropanol, t-butanol, or heavier, unusual or sterically hindered alcohols having a more predictable and slow reactivity. In some embodiments, the reactant may include a low viscosity or gelled solution to react with the alkali metal. In some embodiments, the water or water solution is contained on or in a carrier, such as a sponge, a porous body, or an absorbent polymer substrate. In some embodiments, the absorbent polymer substrate may be a hydrogel including a cross-linked hydrophilic synthetic polymer. In some embodiments, the reactant may include a triglyceride, an anhydrous foam, or a compound with a counter ion that produces upon reacting with sodium or related metals or alloys a compound selected from sodium alginate, sodium difluoride, sodium fluorosilicate, sodium metaborate, sodium paraperiodate, sodium stearate, sodium zirconium glycolate, and sodium perrhenate ($NaReO_4$) in anhydrous ethanol. The addition of sodium or other alkali metals will produce nonahydridorhenate. These are well-behaved reactions that yield inert salts. In some embodiments, the rhenium (Rh) compound may be replaced with more affordable substances such as with technetium (Tc) or manganese (Mn).

Further, in some embodiments, the kit may include a mechanism to receive water from an external source. In some embodiments, the reactant may be a compound with a counter ion that produces upon reacting with sodium a compound selected from sodium alginate ($NaC_6H_7O_6$), potassium difluoride ($KHF_2$), sodium difluoride ($NaHF_2$), sodium fluorosilicate ($Na_2SiF_6$), sodium metaborate ($NaBO_2$), sodium paraperiodate ($Na_3H_2IO_6$), sodium stearate ($NaOOCC_{17}H_{35}$), and sodium zirconium glycolate ($NaZrH_3 (H_2COCOO)_3$).

In some embodiments, the mechanism to receive water from an external source is a water or moisture-permeable polymer membrane, such as that indicted at 134 in FIG. 6. In addition to water or a solution of water and salt, solutions that may be used to limit the rate of the chemical reaction (Eq. 1) may include: propylene glycol (PG), alcohol, or high molar NaOH(aq) such as 10M NaOH, which slowly reacts with the sodium in a controlled manner.

Additionally, in some embodiments, the reactant may include carbon dioxide to form a carbonate of the alkali metal. The $CO_2$ may be in gaseous form or at least one compartment could be filled with a substance that releases carbon dioxide. Additionally, carbon tetrachloride and dichloromethane react vigorously with sodium and could be used to expend the used sodium.

In some embodiments, it may be beneficial to neutralize the products following the alkali metal reactions (cf. Eq. 1). Highly basic alkali hydroxides (e.g., NaOH, cf. Eq. 1) are caustic and may be a hazardous challenge to dispose of. Accordingly, some embodiments may include buffers, acids, or similar compounds in the reactant solution, to neutralize or control the reaction products (e.g., right hand side of Eq. 1).

One or more walls of the first cavity may include a membrane 134 (FIG. 6) that is selectively permeable to hydrogen. Such semi-permeable membrane can be polymeric membranes, porous membranes, dense metal membranes, or ion-conductive membranes.

Exemplary porous membranes include ceramic, carbon, and metallic membranes. Exemplary polymer membranes include: aromatic polyimides, polysulfone, cellulose acetate, polyethylene, and tetrabromopolycarbonate. Exemplary dense metal membranes include palladium and palladium-based alloy membranes. The hydrogen-permeable membrane can also be a hybrid membrane of nanoparticles dispersed in a polymer matrix, such as those described, for example, in Pulyalina A., et al., Polymers, 10(8): 828 (2018). Some embodiments allow hydrogen to escape while retaining water vapor or steam. In some embodiments, the alkali patch may be partially or totally immersed in the reactant (e.g., a PG solution). Some embodiments include environmental control within the container so as to provide a high humidity level. For the latter, a membrane or container that vented hydrogen at a higher rate than water vapor or steam may be desirable.

In one embodiment, water vapor enters the first cavity of the pouch and the reaction with the alkali metal proceeds (cf. Eq. 1). Hydrogen exits the pouch through the membrane or material that is hydrogen-permeable, and the alkali metal then oxidizes, leaving behind a high molar hydroxide hydrate, a crust, or layer of alkali hydroxide (e.g., NaOH cf. Eq. 1) on the used patch, which is safely sealed in the first cavity. In another embodiment, the hydrogen-permeable membrane has a permeation or diffusion rate for hydrogen that is at least about 10%, 20%, 25%, 30%, 35%, 40%, 50%, 60%, 75%, or higher than the permeation rate for water vapor or steam.

In some embodiments, at least the first cavity in the container may include a wall wherein at least a portion of the wall includes a hydrogen-permeable membrane or material (e.g., a synthetic polymer such as those mentioned above, and similar). In some embodiments, the semi-permeable membrane may also be permeable to water vapor or steam. The semi-permeable membrane may be disposed on a bottom wall of the container. The hydrogen released by the interaction between the reactant and the alkali metal may then egress freely from the container through the hydrogen-permeable membrane and be released into the atmosphere. The sealed container including the used patch may then be safely discarded using regular procedures. In some embodiments, the container also includes a source of water or a mechanism to receive water from an external source of water (e.g., the reaction products on the left-hand side of Eq. 1). In one embodiment, the used patch is exposed to water or an aqueous solution in a manner that limits the availability of water for reaction with the alkali metal or alloy, thus avoiding an explosive regime. In some embodiments, the reactant may include a membrane with a pre-selected diffusion gradient that slowly passes water (in liquid or vapor form) across to the cavity that includes the used patch. In some embodiments, the reactant includes an aqueous solution, such as a propylene glycol (PG)+water, salt+water, or alcohol+water. In some embodiments, the reactant may include a sponge that entrains water and slowly allows it to ingress into the cavity at a limited rate to provide for a controlled reaction.

In some embodiments, the reactant may include water or a water solution embedded in a sintered metal, a porous polymer, a porous plastic, or an absorbent polymer substrate (e.g., a hydrogel including a cross-linked hydrophilic synthetic polymer). More specifically, the sintered metal forms a rate limiting interface between the reactant solution and the alkali metal in the used patch. Further, because the metal has a relatively high thermal mass, the sintered metal could control the temperature of the reacting alkali metal below its melting point and below the auto-ignition temperature of hydrogen. The sintered metal or plastic material or combinations thereof may provide a torturous/porous path to limit the rate of water ingress into the cavity that contains the used patch. In some embodiments, the reactant may include beads, a film or sheet of any combination of hydrogel, absorbent or super-absorbent polymer, polyvinyl alcohol (PVA), silicone, or any suitable substrate that contains water or an aqueous solution.

In some embodiments, the reactant may include a solution of propylene glycol (PG). Propylene glycol has the benefit of being miscible with water. It is also non-flammable and safe to use. In some embodiments, the reactant may include a 100% PG solution, or any other ratio of PG/H$_2$O so as to effectively dissolve the patch. For embodiments including a patch having an alkali metal foil sheet (e.g., between about 0.0254 mm to 1.3 mm of metal or alloy, or between about 0.1 mm to 0.3 mm), it may take approximately 30 minutes to 24 hours to completely dissolve the alkali when immersed in a 100% PG solution. Dissolution of the alkali layer in the used patch occurs faster when the amount of water in the aqueous PG solution increases. In some embodiments, it may be desirable to maintain the level of water in the aqueous PG solution to less than approximately 10% to avoid generating too much heat and the formation of small metallic beads due to melting of the alkali metal. When alkali metal beads float to the surface of the solution, they continued to react with the solution, air, and water vapor, and in some cases may ignite the evolved hydrogen.

In some embodiments, the concentration of the PG/water solution may be adjusted (e.g., "tuned") to obtain a desirable reaction rate. For example, in some embodiments, the concentration of the PG/water solution can be tuned such that the rate of formation of hydrogen is no faster than the rate at which the hydrogen egresses from the container. Hydrogen is a very small molecule and is therefore difficult to contain. Standard containers, such as a polyethylene bag with a slidable seal (e.g., Ziploc) or a sealable flap, may successfully contain the used patch and the solvent, and allow the hydrogen to pass through (or membranes, or Tyvek bags can be used as described above). However, when the reaction is allowed to proceed too quickly, hydrogen may form at a rate that exceeds the egress rate from the container. Accordingly, in some embodiments, a careful selection of the ratio of PG and water in solution may slow hydrogen production to a rate that it is matched by the egress rate from the container.

In some embodiments, the reactant, or at least a portion of the disposal kit may include a color changing material that indicates when the reaction with the alkali metal is complete. More generally, the reactant or a portion of the disposal kit may include a material that changes physically in a perceptible way when the reaction is complete. The physical change could be triggered by heat, by pH of a solution or the reaction products contained therein, etc. The color change could indicate to a user when the reaction is complete and when it is safe to dispose of the kit.

In some embodiments, the disposal kit may include an excess of a solution having a high thermal capacity or the container may include at least a portion of a wall made of a metal or other material with a high thermal capacity.

In some embodiments, the disposal kit may include a label or a leaflet (e.g., stamped on the outside of one of the walls, or loosely placed inside the container, or attached through a string). The label or leaflet may include a set of instructions for use 136. In some embodiments, the instructions may be directly printed on the container or on a material that is disposed on an adhesive portion of the used patch.

Figure 7:
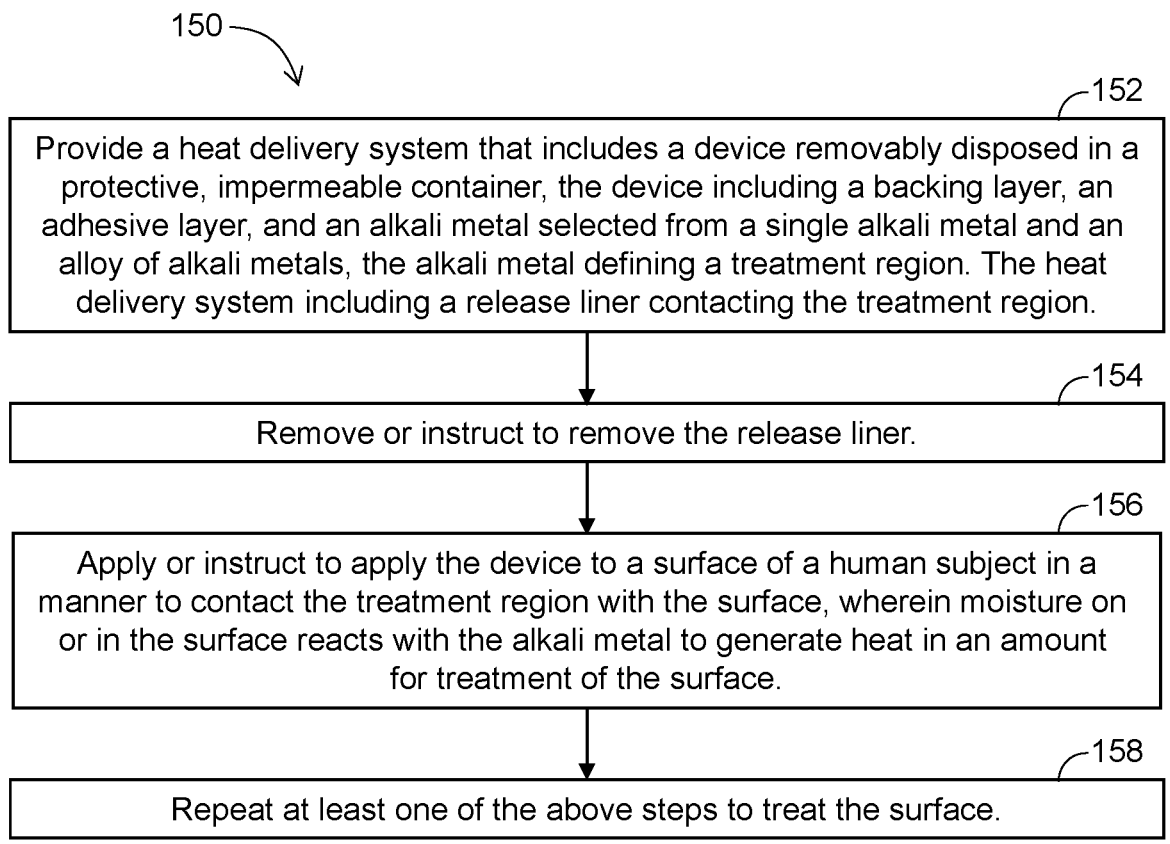
FIG. 7 is a flow chart illustrating steps in a method for a medical or cosmetic treatment using a heat generating device, according to some embodiments.

FIG. 7 is a flow chart illustrating steps in a method 150 for a medical or cosmetic treatment applying heat to a tissue, according to some embodiments. Method 150 may be performed using any one of the devices consistent with the present disclosures, such as a wearable patch. In some embodiments, method 150 includes the use of systems and kits including a wearable device, a storage container, a disposal container, a solvent, and a reagent, as disclosed herein. Further, in some embodiments, methods consistent with the present disclosure may include one or more steps as disclosed herein, performed in any order, sequentially, simultaneously, repeatedly, or partially overlapping in time.

Step 152 includes providing a heat delivery system that includes a device removably disposed in a protective, impermeable container. The device may include a backing layer, an adhesive layer, and an alkali metal selected from a single alkali metal and an alloy of alkali metals. The alkali metal defines a treatment region. In some embodiments, the heat delivery system includes a release liner contacting the treatment region.

Step 154 includes removing or instructing to remove the release liner.

Step 156 includes applying or instructing to apply the device to a treatment site on a surface of a subject. For example, the treatment site can be a skin or mucosal surface of a human subject. Applying the device to the surface causes contact of the treatment region on the device with the surface to be treated. Moisture on or in the surface to be treated (e.g., skin, mucosal tissue) reacts with the alkali metal to generate heat in an amount for treatment. In one embodiment, the treatment is to reduce or eliminate the production of sweat from a skin surface on the human subject.

The method optionally includes step 158 of repeating steps 152, 154 or 156 one or more times at a time subsequent to the initial steps of providing, removing and applying. In one embodiment, the step of repeating is at a time subsequent to the initial steps of one day, two days, three days, four days, five days, six days, seven days, two weeks, three weeks, four weeks, six weeks, eight weeks, ten weeks, or twelve weeks.

In one embodiment, the method illustrated in FIG. 7 is for use in treating hyperhidrosis, wherein treatment with the device reduces or eliminates production of sweat from glands underlying a skin treatment site.

In one embodiment, the amount of heat generated upon application of the device to a surface for treatment is controlled by, is proportional to, and/or is limited by an amount of water at the point of contact. In an embodiment, the exothermic reaction stops when the alkali metal (e.g., sodium free metal, potassium free metal, an alloy of free alkali metals) is fully consumed, thus the amount of heat generated can be directly calculated and controlled by the amount of metal involved in the reaction. In an embodiment, the exothermic reaction stops when the water at the treatment surface is consumed. The amount of heat generated is controllable by the amount of alkali metal and/or by the amount of water available for reaction with the alkali metal.

As used herein, the phrase "at least one of" preceding a series of items, with the terms "and" or "or" to separate any of the items, modifies the list as a whole, rather than each member of the list (e.g., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

To the extent that the term "include," "have," or the like is used in the description or the claims, such term is intended to be inclusive in a manner similar to the term "include" as "include" is interpreted when employed as a transitional word in a claim. The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

The subject matter of this specification has been described in terms of particular aspects, but other aspects can be implemented and are within the scope of the following claims. For example, while operations are depicted in the drawings in a particular order, this should not be understood as requiring that such operations be performed in the particular order shown or in sequential order, or that all illustrated operations be performed, to achieve desirable results. The actions recited in the claims can be performed in a different order and still achieve desirable results. As one example, the processes depicted in the accompanying figures do not necessarily require the particular order shown, or sequential order, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products. Other variations are within the scope of the following claims.

In one aspect, a method may be an operation, an instruction, or a function and vice versa. In one aspect, a claim may be amended to include some or all of the words (e.g., instructions, operations, functions, or components) recited in other one or more claims, one or more words, one or more sentences, one or more phrases, one or more paragraphs, and/or one or more claims.

The foregoing description is intended to illustrate various aspects of the instant technology. It is not intended that the examples presented herein limit the scope of the appended claims. The invention now being fully described, it will be apparent to one of ordinary skill in the art that many changes and modifications can be made thereto without departing from the spirit or scope of the appended claims.

To illustrate the interchangeability of hardware and software, items such as the various illustrative blocks, modules, components, methods, operations, instructions, and algorithms have been described generally in terms of their functionality. Whether such functionality is implemented as hardware, software, or a combination of hardware and software depends upon the particular application and design constraints imposed on the overall system. Skilled artisans may implement the described functionality in varying ways for each particular application.

As used herein, the phrase "at least one of" preceding a series of items, with the terms "and" or "or" to separate any of the items, modifies the list as a whole, rather than each member of the list (e.g., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The word "exemplary" is used herein to mean "serving as an example, instance, or illustration." Any embodiment described herein as "exemplary" is not necessarily to be construed as preferred or advantageous over other embodiments. Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. Relational terms such as first and second and the like may be used to distinguish one entity or action from another without necessarily requiring or implying any actual such relationship or order between such entities or actions. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description. No claim element is to be construed under the provisions of 35 U.S.C. § 112, sixth paragraph, unless the element is expressly recited using the phrase "means for" or, in the case of a method claim, the element is recited using the phrase "step for."

While this specification contains many specifics, these should not be construed as limitations on the scope of what may be described, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially described as such, one or more features from a described combination can in some cases be excised from the combination, and the described combination may be directed to a subcombination or variation of a subcombination.

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the described subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately described subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirements of the applicable patent law, nor should they be interpreted in such a way.

What is claimed is:

1. A device, comprising:
    a backing layer having opposing sides, the backing layer impermeable to water, oxygen, or both;
    an adhesive layer in contact with a first side of the backing layer;
    an alkali metal selected from a single alkali metal and an alloy of multiple alkali metals, the alkali metal in contact with at least a portion of the adhesive layer on the first side of the backing layer to define a treatment region, wherein the alkali metal is in the form of a foil having a thickness of between about 0.0254 mm and 2.54 mm (0.001 in to 0.10 in) and is configured to contact a treatment site to generate heat; and
    a release liner in contact with the adhesive layer and the treatment region.

2. The device of claim 1, wherein the treatment region has a length and a width or a diameter, and the backing layer has a length and a width or a diameter that is greater than the length and width or the diameter of the treatment region.

3. The device of claim 1, wherein the release liner has a length and a width or a diameter that is greater than the length and width or the diameter of the treatment region.

4. The device of claim 1, wherein the release liner has a length and a width or a diameter that is greater than the length and width or the diameter of the backing layer.

5. The device of claim 1, wherein the release liner has a length and a width or a diameter that is greater than the length and width or the diameter of the adhesive layer.

6. The device of claim 1, wherein the release liner and the backing layer have essentially the same length and width or essentially the same diameter, in both cases greater than the length and width or the diameter of the treatment region.

7. The device of claim 1, wherein the release liner (i) is in contact with the adhesive layer and (ii) covers the treatment region.

8. The device of claim 1, wherein the release liner extends to or beyond the boundaries of the adhesive layer and covers the treatment region.

9. The device of claim 1, wherein a lift tab is created by insertion of a material between an edge portion of the adhesive layer and the release liner.

10. The device of claim 9, wherein the lift tab material has opposing sides, wherein one of the opposing sides is coated with a non-adherent material for the adhesive layer.

11. The device of claim 9, wherein the lift tab material has opposing sides, wherein one of the opposing sides is coated with an adherent material for the adhesive layer.

12. The device of claim 1, wherein the backing layer is transparent.

13. The device of claim 12, wherein the backing layer is a transparent, adhesive coated polyolefin.

14. The device of claim 13, wherein the backing layer polyolefin is polyethylene and the adhesive is an acrylate adhesive.

15. The device of claim 1, wherein the alkali metal is selected from pure sodium, pure potassium and an alloy of sodium and potassium.

16. The device of claim 1, wherein the alkali metal and the alloy are not salts or oxides.

17. The device of claim 1, wherein the alkali metal is a continuous layer.

18. The device of claim 1, wherein the adhesive layer is coated on the first side of the backing layer, and wherein the adhesive layer is a pressure sensitive adhesive layer.

19. The device of claim 18, wherein the alkali metal is adhered to the pressure-sensitive adhesive layer.

20. The device of claim 1, wherein the treatment region has a geometry and the backing layer has a geometry, and the treatment region geometry is different from the backing layer geometry.

21. The device of claim 1, wherein the treatment region has an oval geometry and the backing layer has a rectangular geometry.

22. The device of claim 1, where in the treatment region has an area and the backing layer has an area, and the treatment region area is at least 10% smaller than the backing layer area.

23. A heat delivery system, comprising:
    a protective, impermeable container; and
    the device of claim 1 removably disposed in the protective, impermeable container.

24. A kit, comprising
    a heat delivery system comprising the device of claim 1 removably disposed in a protective, water-impermeable container; and
    a means for disposal of the device.

25. The device of claim 1, wherein the adhesive layer comprises a first portion and a second portion, wherein the alkali metal is in contact with the first portion to define the treatment region and the second portion extends beyond the treatment region, and wherein the release liner is in contact with the second portion of the adhesive layer.

26. A device, comprising:
- an impermeable, backing layer;
- an adhesive layer in contact with the backing layer;
- an alkali metal selected from a single alkali metal and an alloy of multiple alkali metals, the alkali metal in contact with at least a portion of the adhesive layer to define a treatment region; and
- a release liner in contact with the adhesive layer and the treatment region,
- wherein the backing layer has opposing sides, and the adhesive layer is coated on one side of the backing layer,
- wherein the adhesive layer is a pressure sensitive adhesive layer, and
- wherein the alkali metal is on or embedded in an adhesive matrix that is in contact with the pressure-sensitive layer.

* * * * *